US010329384B2

(12) United States Patent
Hansen et al.

(10) Patent No.: US 10,329,384 B2
(45) Date of Patent: Jun. 25, 2019

(54) SILICONE-POLYETHER COPOLYMERS, ADHESIVES AND MEDICAL ARTICLES COMPRISING SAME, AND METHODS OF MAKING SAME

(71) Applicant: 3M INNOVATIVE PROPERTIES COMPANY, St. Paul, MN (US)

(72) Inventors: Richard G. Hansen, Mahtomedi, MN (US); James P. DiZio, St. Paul, MN (US); Junkang Liu, Woodbury, MN (US); David S. Hays, Woodbury, MN (US); Deena M. Conrad-Vlasak, Midland, MI (US); Timothy A. Peterson, Lino Lakes, MN (US); Sarah A. Sykora, New Richmond, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 110 days.

(21) Appl. No.: 15/025,740

(22) PCT Filed: Sep. 24, 2014

(86) PCT No.: PCT/US2014/057182
§ 371 (c)(1),
(2) Date: Mar. 29, 2016

(87) PCT Pub. No.: WO2015/048109
PCT Pub. Date: Apr. 2, 2015

(65) Prior Publication Data
US 2016/0215100 A1 Jul. 28, 2016

Related U.S. Application Data

(60) Provisional application No. 61/884,464, filed on Sep. 30, 2013.

(51) Int. Cl.
| | |
|---|---|
| *A61K 9/70* | (2006.01) |
| *C09J 183/12* | (2006.01) |
| *A61K 31/167* | (2006.01) |
| *A61L 24/00* | (2006.01) |
| *C08G 77/46* | (2006.01) |
| *A61K 47/34* | (2017.01) |
| *A61F 13/02* | (2006.01) |
| *A61L 15/58* | (2006.01) |
| *A61L 24/04* | (2006.01) |

(52) U.S. Cl.
CPC .......... *C08G 77/46* (2013.01); *A61F 13/0253* (2013.01); *A61K 9/7069* (2013.01); *A61K 31/167* (2013.01); *A61K 47/34* (2013.01); *A61L 15/58* (2013.01); *A61L 24/0015* (2013.01); *A61L 24/046* (2013.01); *C09J 183/12* (2013.01); *A61L 2300/208* (2013.01); *A61L 2300/404* (2013.01)

(58) Field of Classification Search
CPC ... C08G 77/46; A61F 13/0253; A61K 31/167; A61K 9/7069; A61K 47/34; A61L 15/58; A61L 24/0015; A61L 24/046; C09J 183/12
See application file for complete search history.

(56) References Cited

U.S. PATENT DOCUMENTS

| | | | |
|---|---|---|---|
| 2,532,011 | A | 11/1950 | Dahlquist |
| 2,607,711 | A | 8/1952 | Hendricks |
| 2,676,182 | A | 4/1954 | Daudt |
| 3,318,852 | A | 5/1967 | Dixon |
| 3,502,497 | A | 3/1970 | Crocker |
| 3,627,851 | A | 12/1971 | Brady |
| 3,772,247 | A | 11/1973 | Flannigan |
| 3,890,269 | A | 6/1975 | Martin |
| 4,241,198 | A | 12/1980 | Kobayashi |
| 4,661,577 | A | 4/1987 | Lane |
| 4,707,531 | A | 11/1987 | Shirahata |
| 4,728,571 | A | 3/1988 | Clemens |
| 4,774,310 | A | 9/1988 | Butler |
| 4,849,224 | A | 7/1989 | Chang |
| 4,855,294 | A | 8/1989 | Patel |
| 4,935,484 | A | 6/1990 | Wolfgruber |
| 5,026,890 | A | 6/1991 | Webb |
| 5,032,460 | A | 7/1991 | Kantner |
| 5,110,890 | A | 5/1992 | Butler |
| 5,202,190 | A | 4/1993 | Kantner |

(Continued)

FOREIGN PATENT DOCUMENTS

| | | | |
|---|---|---|---|
| JP | 2-36234 | | 2/1990 |
| WO | 95/03354 | * | 2/1995 |

(Continued)

OTHER PUBLICATIONS

Encyclopedia of Polymer Science and Engineering, "Scattering to Structural Foams", 1989, vol. 15, pp. 265-270.
Fang et al. 2006. *Applied Surface Science.* 253:2978-2983. "Microphase separation behavior on the surfaces of PET-MDI-PDMS multiblock copolymer coatings".
International search Report for PCT International Application No. PCT/US2014/057182 dated Dec. 1, 2014, 4 pages.

*Primary Examiner* — Alma Pipic
(74) *Attorney, Agent, or Firm* — Jeffrey M. Olofson (57) ABSTRACT

Silicone-polyether copolymers, adhesives and medical articles comprising same, and methods of making same. The silicone-polyether copolymer composition can include a backbone composition having a first (silicone) segment and a second (polyether) segment connected randomly via at least one of an oxamide linkage and a urea linkage. The method of making the silicone-polyether copolymer composition can include combining: a) a first (silicone) precursor; b) a second (polyether) precursor; and c) at least one of a diisocyanate and an oxalate compound.

13 Claims, 1 Drawing Sheet

(56) References Cited

U.S. PATENT DOCUMENTS

| | | |
|---|---|---|
| 5,214,119 A | 5/1993 | Leir |
| 5,248,739 A | 9/1993 | Schmidt |
| 5,262,558 A | 11/1993 | Kobayashi |
| 5,276,122 A | 1/1994 | Aoki |
| 5,290,615 A | 3/1994 | Tushaus |
| 5,302,685 A | 4/1994 | Tsumura |
| 5,319,040 A | 6/1994 | Wengrovious |
| 5,356,706 A | 10/1994 | Shores |
| 5,489,624 A | 2/1996 | Kantner |
| 5,512,650 A | 4/1996 | Leir |
| 5,516,581 A | 5/1996 | Kreckel |
| 5,750,630 A | 5/1998 | Sengupta |
| 6,355,759 B1 | 3/2002 | Sherman |
| 6,441,118 B2 | 8/2002 | Sherman |
| 6,664,359 B1 | 12/2003 | Kangas |
| 7,371,464 B2 | 5/2008 | Sherman |
| 7,501,184 B2 | 3/2009 | Leir |
| 2003/0091620 A1* | 5/2003 | Fikstad ............ A61K 9/0014 424/449 |
| 2004/0013629 A1 | 1/2004 | Brandt |
| 2008/0318058 A1 | 12/2008 | Sherman |
| 2011/0071268 A1* | 3/2011 | Hays et al. |

FOREIGN PATENT DOCUMENTS

| | | |
|---|---|---|
| WO | WO 1995-06691 | 3/1995 |
| WO | WO 96/34029 | 10/1996 |
| WO | WO 2007/075802 | 7/2007 |
| WO | WO 2011-034839 | 3/2011 |

\* cited by examiner

SILICONE-POLYETHER COPOLYMERS, ADHESIVES AND MEDICAL ARTICLES COMPRISING SAME, AND METHODS OF MAKING SAME

CROSS REFERENCE TO RELATED APPLICATIONS

This is a national stage filing under 35 U.S.C. § 371 of International Application No. PCT/US2014/057182, filed Sep. 24, 2014, which claims the benefit of U.S. Provisional Application No. 61/884,464, filed Sep. 30, 2013, the disclosure of which is incorporated herein by reference in its entirety.

FIELD

The present disclosure generally relates to a silicone polyether copolymer composition, a pressure-sensitive adhesive comprising the silicone polyether copolymer, and methods of making same.

BACKGROUND

Medical adhesives can have many uses, including securing wound dressings, medical devices (e.g., catheters) surgical drapes, tapes, sensors, and the like, as well as skin sealant and liquid sutures, etc.

Pressure-sensitive adhesives have been used for a variety of marking, holding, protecting, seating, and masking purposes. Pressure-sensitive adhesive can also be useful in the field of skin or medical adhesives, e.g., for use in wound dressings, or the like. The living, sensitive, low surface energy and highly textured surface of skin can present difficulties in adhesion, and the wide variation in the skin surface from individual to individual and from location to location on the same individual can exacerbate these difficulties.

Although some existing silicone adhesives are attractive for skin adhesion due to their inherent good biocompatibility, low surface energy, low glass transition temperature, and high breathability (e.g., high moisture vapor transmission), those existing silicone adhesives are hydrophobic and thus lack of the capability of fluid management and lack of the compatibility to hydrophilic additives.

SUMMARY

Pressure-sensitive adhesives generally require crosslinking for higher adhesion performance, which is typically achieved through on-web curing processes, such as thermal heating processing and/or radiation processing (e.g., electron beam processing), to cure the adhesive. That is, some existing pressure-sensitive adhesives are required to go through a curing process while or after the pressure-sensitive adhesive is being formed and/or applied to an underlying substrate. However, in some cases, such curing processes can be destructive to at least a portion of the composition, such as various excipients or active agents that may be added to the composition. In addition, some existing silicone pressure-sensitive adhesives are incompatible with various active ingredients, especially hydrophilic active ingredients, and thus, are unable to form stable compositions. Therefore, the resulting compositions can be ineffective for delivering or producing the desired functions and/or properties.

The present disclosure generally relates to a copolymer composition, a pressure-sensitive adhesive comprising the copolymer composition, and methods of making same.

Generally, the copolymer compositions and pressure-sensitive adhesives of the present disclosure do not require on-web curing processes that may be destructive to at least a portion of the copolymer composition, such as an excipient or active agent that has been incorporated to achieve various functions and/or properties. For example, antimicrobial agents can be incorporated in copolymer compositions (or pressure-sensitive adhesive comprising such copolymer compositions) without the antimicrobial agents being phase-separated from the composition or being destroyed by a curing process.

Some aspects of the present disclosure provide a copolymer composition. The copolymer composition can include a copolymer having a backbone composition comprising
a first segment of Formula I:

(I), wherein X is a silicone; and
a second segment of a Formula of II:

(II), wherein Y is a polyether;
wherein W comprises at least one of an oxamide linkage and a urea linkage;
wherein b is an integer of at least 0;
wherein c is an integer of at least 0;
wherein b+c is at least 1;
wherein the first segment and the second segment are connected randomly via Z, wherein Z comprises at least one of an oxamide linkage and a urea linkage; and
wherein the copolymer includes at least one of the first segment and at least one of the second segment.

Some aspects of the present disclosure provide a method of making a copolymer composition. The method can include combining:
a) a first precursor of Formula VII:

(VII), wherein X is a silicone;
b) a second precursor of Formula VIII:

(VIII),

Y is a polyether;
wherein b is 0 or greater;
wherein c is 0 or greater;
wherein b+c is at least 1;
wherein W comprises at least one of an oxamide linkage or a urea linkage; and
c) at least one of a diisocyanate and an oxalate compound.

Other features and aspects of the present disclosure will become apparent by consideration of the detailed description and accompanying drawings.

DETAILED DESCRIPTION

Before any embodiments of the present disclosure are explained in detail, it is understood that the invention is not limited in its application to the details of use, construction, and the arrangement of components set forth in the following description or illustrated in the following drawings. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

The present disclosure generally provides a silicone-polyether composition (e.g., an elastomer) comprising a copolymer of a first silicone segment and a second polyether segment. At least one of the silicone segment and the polyether segment can be chain-extended with an oxamide linkage and/or a urea linkage. In the composition, the silicone segment (i.e., which can be chain-extended with an oxamide linkage and/or a urea linkage, e.g., to form a chain-extended silicone diamine) and the polyether segment (i.e., which can be chain-extended with an oxamide linkage and/or a urea linkage, e.g., to form a chain-extended polyether diamine) can be connected randomly via an oxamide linkage and/or a urea linkage.

Chain extension of the silicone and/or the polyether (e.g., to form precursor diamines that are used to form the copolymers of the present disclosure) can provide non-hydrogen bonding, higher molecular weight silicones (e.g., silicone diamines) and/or polyethers (e.g., polyether diamines), respectively. Such higher molecular weight precursors (i.e., silicone and/or polyether) can then be used to make the silicone-polyether copolymers of the present disclosure, which exhibit special properties, at least partly due to the resulting blocks of non-hydrogen bonding portions.

Advantageously, the composition of the present disclosure can carry and deliver active agents such as antimicrobials and drugs, as well as excipients, and thus, in some embodiments, can provide antimicrobial activity. The composition of the present disclosure can also have strong skin adhesion, while providing gentle-to-skin characteristics, including little to no skin irritation, and little to no skin trauma upon removal. The composition of the present disclosure can be useful for pressure-sensitive adhesives (e.g., medical adhesives), medical articles, medical tapes, medical dressings, and combinations thereof.

In some embodiments, the composition can include a silicone-polyether copolymer having a backbone composition having a first (silicone) segment according to the following general Formula I:

(I), where X refers to a silicone; and
a second (polyether) segment according to the following general Formula II:

(II), where Y refers to a polyether; and further where:
W represents at least one of an oxamide linkage and a urea linkage;
b is an integer of at least 0;
c is an integer of at least 0; and
b+c is at least 1.

The first segment and the second segment can be connected randomly via Z, and Z can be at least one of an oxamide linkage and a urea linkage. The copolymer can include at least one of the first segment and the second segment.

The silicone ("X") of the first segment can include, e.g., the following general Formula III:

(III)

where:
each of $R^1$ and $R^2$ is independently selected from hydrogen; an alkyl group having from 1 to 10 carbons; and a phenyl group; and
each of $R^3$ and $R^4$ is independently selected from a linear or branched alkane, having from 1 to 10 carbons, and more specifically, in some embodiments, the first (silicone) segment can include the following general Formula IV:

(IV)

where m in Formulas III and IV is an integer ranging from 10 to 900. In some embodiments, m is an integer ranging from 60 to 850. In some embodiments, m is an integer ranging from 50 to 800. In some embodiments, m is an integer ranging from 200 to 600.

In some embodiments, m is an integer of at least 10; in some embodiments, m is an integer of at least 50; in some embodiments, m is an integer of at least 60; in some embodiments, m is an integer of at least 100; in some embodiments, m is an integer of at least 150; in some embodiments, m is an integer of at least 200. In some embodiments, m is an integer of no greater than 1000; in some embodiments, m is an integer of no greater than 900; in some embodiments, m is an integer of no greater than 850; in some embodiments, m is an integer of no greater than 800; in some embodiments, m is an integer of no greater than 750; in some embodiments, m is an integer of no greater than 600; in some embodiments, m is an integer of no greater than 500.

In some embodiments, the polyether ("Y") of the second segment can include, e.g., the following general Formula V:

(V)

where $R^5$ is a linear or branched alkane, having from 1 to 10 carbons, and
q is an integer ranging from 5 to 500; in some embodiments, ranging from 40 to 500; in some embodiments, ranging from 10 to 250; and in some embodiments, ranging from 20 to 100.

In some embodiments, q is an integer of at least 5; in some embodiments, q is an integer of at least 10; in some embodiments, q is an integer of at least 20; in some embodiments, q is an integer of at least 40; in some embodiments, q is an integer of at least 50. In some embodiments, n is an integer of no greater than 500; in some embodiments, q is an integer of no greater than 400; in some embodiments, q is an integer of no greater than 250; in some embodiments, q is an integer of no greater than 200; in some embodiments, q is an integer of no greater than 150; in some embodiments, q is an integer of no greater than 100.

More specifically, in some embodiments, the second (polyether) segment can include the following general Formula VI:

(VI)

where x is an integer ranging from 2 to 60; and
the sum of w and y is an integer ranging from 2 to 8.

In some embodiments, the molecular weight of the first (silicone) segment of the silicone-polyether copolymer can be at least 5,000. When the molecular weight of the silicone segment is below 5,000, it becomes difficult to obtain enough adhesion to have practical use. In some embodiments, the molecular weight of the first segment can be at least 10,000.

In some embodiments, the molecular weight of the first segment can be no greater than 60,000. When the molecular weight of the first segment exceeds 60,000, the flexibility and adhesion properties can be substantially diminished. In some embodiments, the molecular weight of the first segment can be no greater than 50,000.

In some embodiments, the molecular weight of the second (polyether) segment can be at least 1,000. In some embodiments, the molecular weight of the second segment can range from 1,000 to 40,000.

In some embodiments, the first segment can be generally no greater than 99 wt-%, relative to the total composition. In some embodiments, the first segment can be generally no greater than 90 wt-%, relative to the total composition. In some other embodiments, the first segment can be generally no greater than 80 wt-%, relative to the total composition. In yet other embodiments, the first segment can be generally no greater than 80 wt-%, relative to the total composition. A first segment weight percentage of no greater than 99 wt-% relative to the total composition, can, for example, facilitate excipient loading. For example, in some embodiments, at least 1 wt-% of the second (polyether) segment, can facilitate excipient loading.

In some embodiments, as shown in the Examples, the compositions of the present disclosure can exhibit a microbial load reduction of at least a 1 log, as compared to control (e.g., when tested pursuant to test method JIS Z 2801). In some embodiments, the compositions of the present disclosure can exhibit a microbial load reduction of at least 2 log, as compared to control, and in some embodiments, the compositions of the present disclosure can exhibit a microbial load reduction of at least 3 log, as compared to control.

The copolymer of the present disclosure can be prepared by combining a) a silicone precursor, b) a polyether precursor and c) at least one of a diisocyanate and a diester oxalate compound.

In some embodiments, the method of making the silicone-polyether copolymer comprises combining: a) a first (silicone) precursor of general Formula VII:

(VII), where X is a silicone;
b) a second (polyether) precursor of general Formula VIII:

(VIII), where Y is a polyether;
where W comprises at least one of an oxamide linkage or a urea linkage,
b is 0 or greater; c is 0 or greater,
b+c is at least 1; and
c) at least one of a diisocyanate and an oxalate compound.

The silicone ("X") of the first precursor can include general Formula III. In some embodiments, the silicone of the first precursor can include general Formula IV.

In some embodiments, the silicone of the first precursor can include a diamine-terminated polysiloxane according to Formula IX:

(IX)

where:
$R^6$ is a $C_1$-$C_{10}$ alkane;
$R^7$ is hydrogen, an alkyl group having from 1 to 10 carbons; or a phenyl group;
$R^8$ is an alkyl group having from 1 to 10 carbons; or a phenyl group; and
p is an integer ranging from 10 to 900. In some embodiments, p is an integer ranging from 60 to 850. In some embodiments, p is an integer ranging from 50 to 800. In some embodiments, p is an integer ranging from 200 to 600.

In some embodiments, p is an integer of at least 10; in some embodiments, p is an integer of at least 50; in some embodiments, p is an integer of at least 60; in some embodiments, p is an integer of at least 100; in some embodiments, p is an integer of at least 150; in some embodiments, p is an integer of at least 200. In some embodiments, p is an integer of no greater than 1000; in some embodiments, p is an integer of no greater than 900; in some embodiments, p is an integer of no greater than 850; in some embodiments, p is an integer of no greater than 800; in some embodiments, p is an integer of no greater than 750; in some embodiments, p is an integer of no greater than 600; in some embodiments, p is an integer of no greater than 500.

Useful amine-terminated polysiloxanes can include any diamine-terminated polysiloxanes that fall within Formula IX above and include those amine-terminated polysiloxanes having molecular weights in the range of about 700 to 150,000 g/mole, preferably from about 10,000 to about 60,000 g/mole, and more preferably from about 25,000 to about 50,000 g/mole. Suitable amine-terminated polysiloxanes and methods of manufacturing amine-terminated polysiloxane are disclosed in, e.g., U.S. Pat. No. 3,890,269 (Martin); U.S. Pat. No. 4,661,577 (Lane); U.S. Pat. No. 5,026,890 (Webb et al.), U.S. Pat. No. 5,276,122 (Aoki et al.) U.S. Pat. No. 5,512,650 (Leir et al.) U.S. Pat. No. 6,441,118 (Sherman et al) and U.S. Pat. No. 6,664,359 (Melancon et al.); the disclosures of which are incorporated herein by reference.

Examples of useful diamine-terminated polysiloxanes can include polydimethylsiloxane diamine, polydiphenylsiloxane diamine, polyphenylmethylsiloxane diamine, polydiethylsiloxane diamine, poly(ethyl)methylsiloxane diamine, and mixtures and copolymers thereof.

Suitable diamine-terminated polysiloxanes are commercially available from, for example, Shin Etsu Silicones of America, Inc., Torrance, Calif., and Huls America, Inc. Preferably, the amine-terminated polysiloxanes are substantially pure and prepared as disclosed in U.S. Pat. No. 5,214,119 (Leir et al.). Amine-terminated polysiloxanes having such high purity may be prepared from the reaction of cyclic organosilanes and bis(aminoalkyl)disiloxanes utilizing an anhydrous amino alkyl functional silanolate catalyst such as tetramethylammonium-3-aminopropyldimethyl silanolate, preferably in an amount less than 0.15% by weight based on the weight of the total amount of cyclic organosiloxane with the reaction run in two stages.

The polyether ("Y") of the second precursor can include general Formula V. The polyether ("Y") of the second precursor can include general Formula VI.

In some embodiments, one or both of the silicone ("X") of the first precursor and the polyether ("Y") of second precursor can be chain-extended.

In some embodiments in which the silicone-polyether copolymer of the present disclosure is prepared using a chain-extended polyether (i.e., a "polyether oligomeric precursor"), the polyether oligomeric precursor can comprise general Formula VIII, where Y is a polyether, W comprises at least one of an oxamide group and a urea group, and c is an integer ranging from 1 to 30.

In some embodiments in which the silicone-polyether copolymer of the present disclosure is prepared using a chain-extended silicone (i.e., a silicone oligomeric precursor), the silicone oligomeric precursor can comprise general Formula VII, where X is a silicone, W comprises at least one of an oxamide group and a urea group, and b is an integer ranging from 1 to 30.

In some embodiments, the oxamide group can include the following general Formula X:

(X)

In some embodiments, the urea group can include the following general Formula XI:

(XI)

where B is an aliphatic or aromatic compound.

By way of example only, in some embodiments, the chain extended second (polyether) precursor (i.e., a polyether oligomer) can be prepared by reacting a polyether precursor of general Formula XII:

(XII)

with a less than molar amount of an oxalate compound, such as diester oxalate, to form a chain-extended second (polyether) precursor (or "polyether oligomer" or "polyether oligomeric precursor") as illustrated in Scheme 1 below, where n is at least 1, and where the chain-extended second (polyether) precursor is chain-extended by one or more oxamide linkages.

Scheme 1:

In such embodiments, the chain-extended (i.e., oxamide-extended in this illustrative embodiment) second (polyether) precursor resulting from Scheme 1 can react with a first (silicone) precursor (i.e., the diamine of Formula IV, by way of example only) to make a silicone-polyether copolymer according to the present disclosure, as shown in Scheme 2.

Scheme 2:

where PDMS is polydimethylsiloxane.

Schemes 1 and 2 are illustrated by way of example only to represent one embodiment of the present disclosure.

In some embodiments (e.g., in embodiments in which it is desired for the copolymer to have pressure-sensitive adhesive properties), the molecular weight of the first (silicone) precursor can be generally at least 5,000 Daltons. When the molecular weight of the first precursor is below 5,000 Daltons, the synthesized copolymer may not exhibit enough adhesive properties to be useful as a pressure-sensitive adhesive. In some embodiments, the molecular weight of the first precursor can be at least 10,000 Daltons. In some other embodiments, the molecular weight of the first precursor can be at least 20,000 Daltons. In yet other embodiments, the molecular weight of the first precursor can be at least 30,000 Daltons.

On the other hand, in some embodiments, the molecular weight of the first precursor can be generally no greater than 60,000 Daltons. When the molecular weight of the first silicone precursor exceeds 60,000 Daltons, the viscosity may be too high, rendering characterization and further synthetic routes difficult. In some other embodiments, the molecular weight of the first precursor can be no greater than 50,000 Daltons. In yet other embodiments, the molecular weight of the first precursor can be generally no greater than 40,000 Daltons.

In some embodiments, the molecular weight of the second (polyether) precursor can be at least 2,000 Daltons.

In some embodiments, the weight ratio of the first precursor to the second precursor can be no greater than 99:1. In some other embodiments, the weight ratio of the first precursor to the second precursor can be no greater than 90:10. In yet other embodiments, the weight ratio of the first precursor to the second precursor can be no greater than 80:20.

In general, when the ratio of the first precursor to the second precursor exceeds 99:1, there may be an insufficient amount of the second precursor for the copolymer to carry and deliver active agents such as antimicrobials and drugs, as well as excipients. On the other hand, in some embodiments, the ratio of the first precursor to the second precursor can be generally at least 60:40. When the ratio of the first precursor to the second precursor is lower than 60:40 (e.g., 50:50), the modulus of the synthesized copolymer is drastically increased and impractical to use as a pressure sensitive adhesive. Some embodiments of the present disclosure provide a pressure-sensitive adhesive that comprises the above-described copolymer composition. Such pressure-sensitive adhesives can be used as adhesive coatings on non-tacky substrates, or backing layers, to provide tapes (e.g., medical tapes), transdermal drug delivery patches, and the like, and/or to reversibly adhere two surfaces.

As mentioned above, some existing pressure-sensitive adhesives require on-web curing, such as electron beam processing ("e-beam processing") to cure the adhesive, and as a result, generally precludes the use of these adhesives for delivery of active agents or certain excipients. Examples of various active agents and excipients that can be employed with the compositions and adhesives of the present disclosure are described below.

The pressure-sensitive adhesives prepared from the compositions of this disclosure provide the desired balance of tack, peel adhesion, and shear holding power.

By way of example, in some embodiments, the pressure-sensitive adhesive of the present disclosure can include a tackifier, a plasticizer, or the like, or combinations thereof.

A tackifier can be added to modify the rheology properties of pressure-sensitive adhesives. A tackifier can also modify properties such as tack, i.e., the ability to stick with finger pressure; adhesion, i.e., the binding force of the adhesive;

and/or cohesive strength (i.e., the ability of adhesive polymers to remove cleanly from the substrate, without leaving adhesive residue on the substrate. The proper tackifier can also lend the adhesive composition sufficient viscous flow properties to bring the adhesive and substrate into intimate contact, thus allowing adhesive bonds to form.

In some embodiments, the tackifier of the present disclosure can include, but is not limited to a silicate tackifier resin, known as an "MQ resin".

MQ silicate resins useful in the present adhesive composition include those composed of the structural units M, D, T, Q, and combinations thereof. For example, MQ silicate resins, MQD silicate resins, and MQT silicate resins that also may be referred to as copolymeric silicate resins and that preferably have a number average molecular weight of about 100 to about 50,000, more preferably about 500 to about 10,000 and generally have methyl substituents. Silicate resins include both nonfunctional and functional resins, the functional resins having one or more functionalities including, for example, silicon-bonded hydrogen, silicon-bonded alkenyl, and silanol.

MQ silicone resins are copolymeric silicone resins having $R^9{}_3SiO_{1/2}$ units (M units) and $SiO_{4/2}$ units (Q units), where $R^9$ is an alkyl or aryl group, and most frequently a methyl group.

Such resins are described in, for example, Encyclopedia of Polymer Science and Engineering, vol. 15, John Wiley & Sons, N.Y., 1989, pp. 265 to 270, and U.S. Pat. No. 2,676,182 (Daudt et al.); U.S. Pat. No. 3,627,851 (Brady); U.S. Pat. No. 3,772,247 (Flannigan); and U.S. Pat. No. 5,248,739 (Schmidt et al.), the disclosures of which patents are incorporated herein by reference. MQ silicone resins having functional groups are described in U.S. Pat. No. 4,774,310 (Butler), which describes silyl hydride groups, U.S. Pat. No. 5,262,558 (Kobayashi et al.), which describes vinyl and trifluoropropyl groups, and U.S. Pat. No. 4,707,531 (Shirahata), which describes silyl hydride and vinyl groups, the disclosures of which are incorporated herein. The above-described resins are generally prepared in solvent. Dried or solventless MQ silicone resins are prepared as described in U.S. Pat. No. 5,319,040 (Wengrovius et al.); U.S. Pat. No. 5,302,685 (Tsumura et al.); and U.S. Pat. No. 4,935,484 (Wolfgruber et al.); the disclosures of which are incorporated herein by reference.

MQD silicone resins are terpolymers having $R^9{}_3SiO_{1/2}$ units (M units) and $SiO_{4/2}$ units (Q units) and $R^9{}_2SiO_{2/2}$ units (D units) as described, e.g., in U.S. Pat. No. 5,110,890 (Butler), the disclosure of which is incorporated herein by reference and Japanese Kokai HE 2-36234.

MQT silicone resins are terpolymers having $R^9{}_3SiO_{1/2}$ units (M units), $SiO_{4/2}$ units (Q units), and $R^9SiO_{3/2}$ units (T units) such as are taught in U.S. Pat. No. 5,110,890, incorporated herein by reference.

Commercially available silicate resins include SR-545, MQ resin in toluene, available from Momentive Inc., Columbus, Ohio; MQOH resins which are MQ silicate resins in toluene, available from PCR Inc., Gainesville, Fla.; MQR-32-1, MQR-32-2, and MQR-32-3 resins which are MQD resin in toluene, available from Shin-Etsu Chemical Co. Ltd., Torrance, Calif.; and PC-403, hydride functional MQ resin in toluene available from Rhone-Poulenc, Latex and Specialty Polymers, Rock Hill, S.C. Such resins are generally supplied in organic solvent and may be employed in compositions of the present disclosure as received. However, these organic solutions of silicate resin may also be dried by any number of techniques known in the art, such as spray drying, oven drying, steam drying, etc. to provide a silicate resin at about 100% nonvolatile content for use in compositions of the present disclosure. Also useful in compositions of the present disclosure are blends of two or more silicate resins.

In adhesive compositions, the MQ tackifying resin can be present in the pressure-sensitive adhesive composition in an amount sufficient to impart a degree of adhesive tack to the dried composition at the use temperature. Generally, the MQ resin is used in amounts of from about 10 to 50 weight percent.

Plasticizers are generally added to soften a material by either softening the final product or to increase the workability of the material before it hardens. Generally, plasticizers work by embedding themselves between the chains of polymers, spacing them apart or increasing the free volume, and thus lowering the glass transition temperature which makes the material more pliant.

In some embodiments, the plasticizers of the present disclosure can include, but are not limited to polyethylene glycol, polypropylene glycol, esters of polyethylene glycol and polypropylene glycol, glycerin, polypropylene glycol-polyethylene oxide copolymer, block copolymers of ethylene oxide and propylene oxide, polyethylene oxide alkylphenyl esters, sorbitol, mannitol, lanolin, lecithin, silicone oil, silicone gum or combinations thereof.

In some embodiments, the plasticizers of the present disclosure can include an excipient. Excipients are typically added to improve efficacy, for example, to enhance drug release from or through the composition. In some embodiments, excipients can include, but are not limited to fatty acid esters, polyols, surfactants, terpenes, glycerol esters, polyethylene glycol esters, amides, sulfoxides, lactams, nonionic surfactants, sorbitan esters, or combinations thereof.

In some embodiments, the silicone-polyether copolymer or the pressure-sensitive adhesive of the present disclosure can include an active agent. In some embodiments, the active agent can include, but is not limited to estradiol, nicotine, nitroglycerine, clonidine, scopolamine, lidocaine, buprenorphine, rivastigmine, donepezil, fentanyl, sufentanil, testosterone, capsaicin, menthol, salicylic acid, oxybutynin, ethinyl estradiol, levonorgestrel, norethindrone, methylphenidate, selegiline, diclofenac, rotigotine, norelgestromin, granisetron, or combinations thereof. Other active agents are identified as drugs or pharmacologically active agents and are also disclosed in detail in U.S. Pat. Nos. 4,849,224 and 4,855,294, which are incorporated herein by reference.

In some embodiments, the active agent can include an antimicrobial agent. In some embodiments, the antimicrobial agent can include, but is not limited to iodine, complexed forms of iodine, chlorhexidine salts, parachlorometaxylenol, triclosan, hexachlorophene, fatty acid esters, phenols, surfactants having a C12-C22 hydrophobe and a quaternary ammonium group, quaternary amines, quaternary silanes, hydrogen peroxide, silver, silver salts, silver oxide, silver sulfadiazine, or combinations thereof.

In some embodiments, the quaternary ammonium salt can include, but is not limited to CHG, PHMB, benzalkonium, benzethonium, polyDADMAC, homopolymers or copolymers comprising pendant quaternized ammonium moieties, or combinations thereof.

In some embodiments, the active agent can include a bioactive agent. In some embodiments, the bioactive agent can include, but is not limited to a protein, an enzyme, a growth factor, a hormone, a biocidal agent, an antiseptic agent, an antibacterial agent, an antifungal agent, an antiviral agent, an anti-histamine, an anti-inflammatory agent, an anti-pruritic agent, a keratolytic agent, an skin-protective agent, a rubefacient, a topical anesthetic, a hemostatic agent, an anti-anginal agent, a vitamin, a nutritional mineral, a water-soluble cellulose compound, collagen, nicotine, or combinations thereof.

In some embodiments, the pressure-sensitive adhesives of the present disclosure can be used in medical articles, medical tapes, medical dressings, and drug-in-adhesive (DIA) transdermal patches.

As used herein, "medical articles" include, but are not limited to, medical tapes, surgical drapes, medical dressings (e.g., intravenous dressings and wound dressings), electrodes, ostomy pouches, transdermal drug delivery patches, first aid bandages, and combinations thereof.

Figure 1:
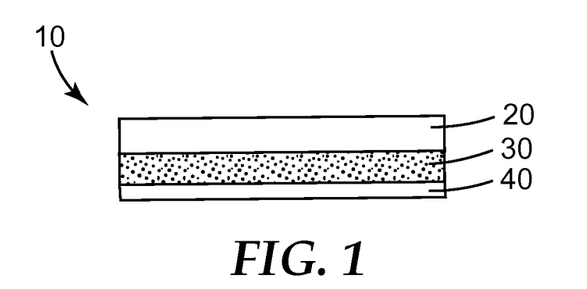
FIG. 1 is a schematic side view of a medical article according to one embodiment of the present disclosure.

FIG. 1 illustrates a medical article 10 according to one embodiment of the present disclosure. As shown in FIG. 1, the medical article 10 can include a medical backing 20, a pressure-sensitive adhesive 30 of the present disclosure, and a release liner 40 in contact with the adhesive to prevent premature adhesion.

The medical backing can include single-layer and multi-layer constructions. Useful backings can include, e.g., a polymeric foam layer, a polymeric film layer, a fabric layer, a nonwoven layer, and combinations thereof, provided such backings have the proper breathable, optical, and mechanical properties.

Potentially useful polymeric backing materials are disclosed in U.S. Pat. No. 5,516,581 (Kreckel et al.) and PCT Publication No. WO 95/06691. Representative examples of potentially useful polymeric backing materials for polymeric foam layers or solid polymeric film layers include polyurethane; polyolefins, e.g., polyethylene, including high density polyethylene, low density polyethylene, linear low density polyethylene, and linear ultra low density polyethylene, polypropylene and polybutylenes; vinyl copolymers, e.g., polyvinyl chlorides, both plasticized and unplasticized, and polyvinyl acetates; olefin copolymers, e.g., ethylene/methacrylate copolymers, ethylene/vinylacetate copolymers, acrylonitrile-butadiene-styrene copolymers, and ethylene/propylene copolymers; acrylic polymers and copolymer; and combinations thereof. Mixtures or blends of any plastic or plastic and elastomer materials, such as polypropylene/polyethylene, polyurethane/polyolefin, polyurethane/polycarbonate, and polyurethane/polyester, can also be used.

Polymeric foams can be selected to optimize tape properties such as conformability and resiliency, which are useful when the tape is to be adhered to surfaces having surface irregularities, e.g., painted wallboard. Conformable and resilient polymeric foams are well suited for applications in which the adhesive tape is to be adhered to surfaces having surface irregularities. Such is the case with a typical wall surface. Polymeric foam layers for use in the backing generally will have a density of about 2 to about 30 pounds per cubic foot (about 32 to about 481 kg/m$^3$), particularly in tape constructions where the foam is to be stretched to effect debonding. Where only one polymeric film or foam layer of a multi-layer backing is intended to be stretched to effect debonding, that layer should exhibit sufficient physical properties and be of a sufficient thickness to achieve that objective.

Polymeric films may be used to increase load bearing strength and rupture strength of the tape. Films are particularly well suited to applications involving adhering smooth surfaces together. A polymeric film layer typically has a thickness of about 10 micrometers (0.4 mil) to about 254 micrometers (10 mils).

In some embodiments, the backing can include an elastomeric material. Suitable elastomeric backing materials include, e.g., styrene-butadiene copolymer, polychloroprene (i.e., neoprene), nitrile rubber, butyl rubber, polysulfide rubber, cis-1,4-polyisoprene, ethylene-propylene terpolymers (e.g., EPDM rubber), silicone rubber, silicone elastomers such as silicone polyurea block copolymers, polyurethane rubber, polyisobutylene, natural rubber, acrylate rubber, thermoplastic rubbers, e.g., styrene-butadiene block copolymers and styrene-isoprene-styrene block copolymers, and thermoplastic polyolefin rubber materials.

Figure 2:
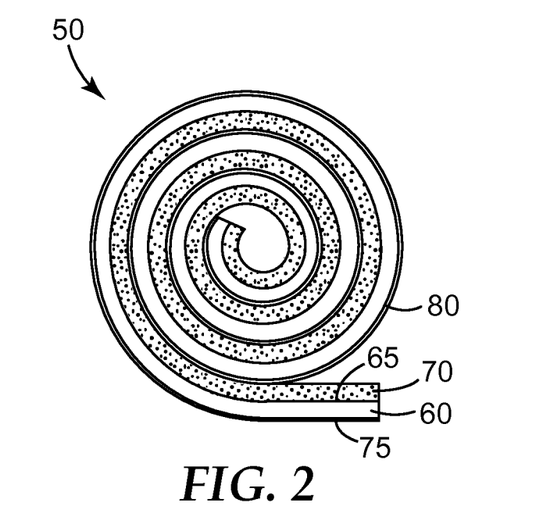
FIG. 2 is a schematic side view of a roll of medical tape according to one embodiment of the present disclosure.

FIG. 2 illustrates a medical tape 50 according to one embodiment of the present disclosure. As shown in FIG. 2, the medical tape 50 can include a medical backing 60 (such as those described above with respect to the medical backing 20 of FIG. 1); a pressure-sensitive adhesive 70 of the present disclosure on a first surface 65 of the backing 60, and a low adhesion backsize coating 80 on a second (i.e., opposite) surface 75 of the backing 60.

When a pressure-sensitive adhesive is coated onto one side of the film, a release coating (e.g., a low adhesion backsize (LAB) coating) can optionally be coated on the opposite face to allow the resultant tape to unwind from itself when wound in a roll or to release when in a pad form. When utilized, the release coating composition should be compatible with the adhesive composition and not degrade the adhesive properties of the tape, such as by being transferred to the adhesive composition.

Release coating compositions for the LAB layer of tapes may include silicone, alkyl, or fluorochemical constituents, or combinations thereof, as the release imparting component. Useful release coating compositions for the invention include silicone containing polymers, such as silicone polyurethanes, silicone polyureas and silicone polyurethane/ureas, such as those described in U.S. Pat. Nos. 5,214,119, 5,290,615, 5,750,630, and 5,356,706, and silicone acrylate grafted copolymers described in U.S. Pat. Nos. 5,032,460, 5,202,190, and 4,728,571. Other useful release coating compositions include fluorochemical containing polymers such as those described in U.S. Pat. No. 3,318,852, and polymers containing long alkyl side chains such as polyvinyl N-alkyl carbamates (e.g., polyvinyl N-octadecyl carbamates) as described in U.S. Pat. No. 2,532,011, and copolymers containing higher alkyl acrylates (e.g., octadecyl acrylate or behenyl acrylate), such as those described in U.S. Pat. No. 2,607,711, or alkyl methacrylates (e.g., stearyl methacrylate) such as those described in U.S. Pat. Nos. 3,502,497 and 4,241,198, where the alkyl side chain includes from about 16 to 22 carbon atoms.

The following embodiments are intended to be illustrative of the present disclosure and not limiting.

EMBODIMENTS

Embodiment 1 is a copolymer composition comprising:
a copolymer having a backbone composition comprising
a first segment of Formula I:

(I), wherein X is a silicone; and
a second segment of a Formula of II:

(II), wherein Y is a polyether;
wherein W comprises at least one of an oxamide linkage and a urea linkage;
wherein b is an integer of at least 0;

wherein c is an integer of at least 0;
wherein b+c is at least 1;
wherein the first segment and the second segment are connected randomly via Z, wherein Z comprises at least one of an oxamide linkage and a urea linkage; and
wherein the copolymer includes at least one of the first segment and at least one of the second segment.

Embodiment 2 is a pressure-sensitive adhesive comprising the composition of embodiment 1, and at least one of a tackifier and a plasticizer.

Embodiment 3 is the pressure-sensitive adhesive of embodiment 2, wherein the pressure-sensitive adhesive comprises a plasticizer.

Embodiment 4 is the pressure-sensitive adhesive of embodiment 3, wherein the plasticizer includes an excipient.

Embodiment 5 is the pressure-sensitive adhesive of embodiments 2-4, further comprising an active agent.

Embodiment 6 is the pressure-sensitive adhesive of embodiment 5, wherein the active agent is selected from estradiol, nicotine, nitroglycerine, clonidine, scopolamine, lidocaine, buprenorphine, rivastigmine, donepezil, fentanyl, sufentanil, testosterone, capsaicin, menthol, salicylic acid, oxybutynin, ethinyl estradiol, levonorgestrel, norethindrone, methylphenidate, selegiline, diclofenac, rotigotine, norelgestromin, granisetron, and combinations thereof.

Embodiment 7 is the pressure-sensitive adhesive of embodiment 5, wherein the active agent includes an antimicrobial agent.

Embodiment 8 is the pressure-sensitive adhesive of embodiment 7, wherein the antimicrobial agent comprises a quaternary ammonium salt.

Embodiment 9 is the pressure-sensitive adhesive of embodiment 8, wherein the quaternary ammonium salt is selected from CHG, PHMB, benzalkonium, benzethonium, polyDADMAC, homopolymers or copolymers comprising pendant quaternized ammonium moieties, and combinations thereof.

Embodiment 10 is the pressure-sensitive adhesive of embodiment 5, wherein the active agent includes a bioactive agent.

Embodiment 11 is the copolymer composition of embodiment 1 or the pressure-sensitive adhesive of embodiments 2-10, wherein the silicone comprises a formula according to Formula IV:

wherein m is an integer ranging from 10 to 900.

Embodiment 12 is the copolymer composition or the pressure-sensitive adhesive of embodiment 11, wherein m is an integer ranging from 66 to 807.

Embodiment 13 is the copolymer composition or the pressure-sensitive adhesive of embodiments 11-12, wherein m is an integer ranging from 50 to 800.

Embodiment 14 is the copolymer composition or the pressure-sensitive adhesive of embodiments 11-13, wherein m is an integer ranging from 200 to 600.

Embodiment 15 is the copolymer composition of embodiments 1 and 11-14 or the pressure-sensitive adhesive of embodiments 2-14, wherein the molecular weight of the first segment is at least 5,000.

Embodiment 16 is the copolymer composition of embodiments 1 and 11-15 or the pressure-sensitive adhesive of embodiments 2-15, wherein the molecular weight of the first segment is at least 10,000.

Embodiment 17 is the copolymer composition of embodiments 1 and 11-16 or the pressure-sensitive adhesive of embodiments 2-16, wherein the molecular weight of the first segment is no greater than 60,000.

Embodiment 18 is the copolymer composition of embodiments 1 and 11-17 or the pressure-sensitive adhesive of embodiments 2-17, wherein the molecular weight of the first segment is no greater than 50,000.

Embodiment 19 is the copolymer composition of embodiments 1 and 11-18 or the pressure-sensitive adhesive of embodiments 2-18, wherein the molecular weight of the second segment is at least 1,000.

Embodiment 20 is the copolymer composition of embodiments 1 and 11-19 or the pressure-sensitive adhesive of embodiments 2-19, wherein the molecular weight of the second segment ranges from 1,000 to 40,000.

Embodiment 21 is the copolymer composition of embodiments 1 and 11-20 or the pressure-sensitive adhesive of embodiments 2-20, wherein the polyether comprises a formula according to Formula VI:

wherein x is an integer ranging from 2 to 60; and
wherein the sum of w and y is an integer ranging from 2 to 8.

Embodiment 22 is the copolymer composition of embodiments 1 and 11-21 or the pressure-sensitive adhesive of embodiments 2-21, wherein the first segment is no greater than 99 wt-%, relative to the total composition of the pressure-sensitive adhesive.

Embodiment 23 is the copolymer composition of embodiments 1 and 11-22 or the pressure-sensitive adhesive of embodiments 2-22, wherein the first segment is no greater than 90 wt-% wt, relative to the total composition of the pressure-sensitive adhesive.

Embodiment 24 is the copolymer composition of embodiments 1 and 11-23 or the pressure-sensitive adhesive of embodiments 2-23, wherein the first segment is no greater than 80 wt-%, relative to the total composition of the pressure-sensitive adhesive.

Embodiment 25 is the copolymer composition of embodiments 1 and 11-24 or the pressure-sensitive adhesive of embodiments 2-24, wherein the first segment is no greater than 70 wt-%, relative to the total composition of the pressure-sensitive adhesive.

Embodiment 26 is the copolymer composition of embodiments 1 and 11-25 or the pressure-sensitive adhesive of embodiments 2-25, wherein the composition further comprises an antimicrobial agent and exhibits a microbial load reduction of at least 1 log, as compared to control, when tested pursuant to JIS Z 2801.

Embodiment 27 is a medical article comprising
a medical backing;
the pressure-sensitive adhesive of any of embodiments 2-26;
and a release liner in contact with the adhesive.

Embodiment 28 is a medical tape, comprising:
a medical backing;
the pressure-sensitive adhesive of any of embodiments 2-26 on a first surface of the backing; and
a low adhesion backsize coating on a second surface of the backing, wherein the second surface of the backing is opposite the first surface.

Embodiment 29 is a method of making a copolymer composition, the method comprising combining:
a) a first precursor of Formula VII:

(VII), wherein X is a silicone;
b) a second precursor of Formula VIII:

(VIII),

Y is a polyether;
wherein b is 0 or greater;
wherein c is 0 or greater;
wherein b+c is at least 1;
wherein W comprises at least one of an oxamide linkage or a urea linkage; and
c) at least one of a diisocyanate and an oxalate compound.

Embodiment 30 is the method of embodiment 29, wherein the silicone comprises a formula according to Formula IV:

(IV)

wherein m is an integer ranging from 10 to 900.

Embodiment 31 is the method of embodiment 30, wherein m is an integer ranging from 66 to 807.

Embodiment 32 is the method of embodiments 30-31, wherein m is an integer ranging from 50 to 800.

Embodiment 33 is the method of embodiments 30-32, wherein m is an integer ranging from 200 to 600.

Embodiment 34 is the method of embodiments 29-33, wherein the polyether comprises a formula according to Formula VI:

(VI)

wherein x is an integer ranging from 2 to 60; and
wherein the sum of w and y is an integer ranging from 2 to 8.

Embodiment 35 is the method of embodiments 29-34, wherein the second precursor is prepared by reacting a polyether oligomer of Formula XII:

(XII)

with a less than molar amount of an oxalate compound.

Embodiment 36 is the method of embodiments 29-35, wherein the molecular weight of the first precursor is at least 5,000.

Embodiment 37 is the method of embodiments 29-36, wherein the molecular weight of the first precursor is at least 10,000.

Embodiment 38 is the method of embodiments 29-37, wherein the molecular weight of the first precursor is no greater than 60,000.

Embodiment 39 is the method of embodiments 29-38, wherein the molecular weight of the first precursor is no greater than 50,000.

Embodiment 40 is the method of embodiments 29-39, wherein the molecular weight of the second precursor is at least 1,000.

Embodiment 41 is the method of embodiments 29-40, wherein the weight ratio of the first precursor to the second precursor is no greater than 99:1.

Embodiment 42 is the method of embodiments 29-41, wherein the weight ratio of the first precursor to the second precursor is no greater than 90:10.

Embodiment 43 is the method of embodiments 29-42, wherein the weight ratio of the first precursor to the second precursor is no greater than 80:20.

Embodiment 44 is the method of embodiments 29-43, wherein the weight ratio of the first precursor to the second precursor is at least 60:40.

Embodiment 45 is the method of embodiments 29-44, wherein the first precursor comprises a formula according to the general formula:

Embodiment 46 is the method of embodiments 29-45, wherein the second precursor comprises a formula according to the general formula:

wherein x is an integer ranging from 2 to 60;
wherein the sum of w and y is an integer ranging from 2 to 8; and
wherein n is at least 1.

The following working examples are intended to be illustrative of the present disclosure and not limiting.

EXAMPLES

Various features and aspects of the present invention are further illustrated by the following examples, but the particular materials and amounts thereof recited in these examples, as well as other conditions and details, should not be construed to unduly limit the present invention.

Materials

Materials utilized for the examples are shown in Table 1.

TABLE 1

Materials List

| Compound | Description | Source |
| --- | --- | --- |
| ED-2003 | Jeffamine ED-2003; polyether diamine based predominantly on a polyethylene glycol backbone of about 2000 molecular weight | Huntsman Corp., The Woodlands, TX |
| XTJ-578 | Jeffamine XTJ-578; polyetherdiamine of about 2000 molecular weight | Huntsman Corp., The Woodlands, TX |
| Bis(trifluoroethyl) oxalate | Prepared as described in U.S. Pat. No. 7,501,184. | 3M, St. Paul, MN |
| PDMS diamine | Polydimethylsiloxane diamine, 33,000 g/mole, prepared as described in U.S. Pat. No. 6,355,759. | 3M, St. Paul, MN |
| IPDI | Isophorone diisocyanate | TCI America, Portland, OR |
| MQ resin | 803 TF MQ Resin, a co-hydrolysis product of tetraalkoxy silane (Q unit) and trimethyl-ethoxy silane (M unit). | Wacker Chemical Corp., Adrian, MI |
| GMIS | Cithrol GMIS 40-LQ-(MV)-monoisostearyl glycerol | Crota Inc., Edison, NJ |
| Glycerol | Glycerol | EMD Chemicals Inc. Gibbstown, NJ |
| SPAN 20 | Sorbitan monolaurate | Alfa Aesar, Ward Hill, MA |
| PEG | Polyethylene glycol, 200 molecular weight | Alfa Aesar, Ward Hill, MA |
| CHG | Chlorhexidine gluconate, 20% w/v in water. | Medichem S.A., Barcelona, Spain |
| H12MDI | Desmodur W, bis-(4-isocyanatocyclohexyl) methane | Bayer Material Science, Pittsburg, PA |
| Lidocaine | Lidocaine | Moehs, Barcelona, Spain |

Test Methods

Peel Test

Adhesion to steel was determined with a method based on ASTM D1000. Briefly, a 2.54 cm wide by 25 cm long sample (adhesive laminated to polyurethane film) was applied to a cleaned stainless steel plate with one pass of a 2 kg roller. An Instron tensile tester (Instron, Norwood, Mass.) was used to peel the sample at 90° at 30 cm/min. The average peel force was recorded in g/2.54 cm.

Microbial Kill

Microbial kill was determined base on test method JIS Z 2801 (Japan Industrial Standards; Japanese Standards Association; Tokyo, JP). A S. aureus (ATCC 6538) bacterial inoculum was prepared in a solution of 1 part nutrient broth (NB) and 499 parts phosphate buffer. A portion of the bacterial suspension (150 ul) was placed onto the surface of a test sample and the inoculated sample was incubated up to 24 hours at 37+/−1° C. After incubation, the test sample was placed into 20 ml of D/E (Dey/Engley) Neutralizing Broth (Difco™, BD, San Jose, Calif.). The number of surviving bacteria in the Neutralizing Broth was determined by using Petrifilm™ AC plates, (3M Company, St. Paul, Minn.). The samples were serially diluted by ten-fold dilutions and each dilution was plated onto the Petrifilm™ plate. Plates were incubated for 48 hours at 37+/−1° C. After incubation, the colonies were counted and the number of surviving bacteria were calculated. Microbial kill was determined by subtracting the log of the number of surviving colonies on the test samples from the log of the number of surviving colonies on a polyester control film.

EXAMPLES

Extended PEG Diamine Preparation

To 700 g ED-2003 was added 660 mL toluene. This mixture was heated to 40° C. and 69 g bis(trifluoroethyl) oxalate was added. This mixture was sealed under argon and heated to 100° C. for 120 minutes. The mixture was removed from heat and mixed on a roller for 4 days at room temperature to produce a 50% solids extended PEG diamine solution. The titrated SAEW (solution amine equivalent weight) was approximately 10,000.

Extended PEG diamines with SAEW of approximately 20,000 and 30,000 were made in a similar manor as shown in Table 2.

TABLE 2

Extended PEG Diamine Preparation

| PEG Diamine | ED-2003 (g) | Bis(trifluoroethyl) oxalate (g) | Toluene (g) | Approximate EW |
|---|---|---|---|---|
| PEGD-1 | 700 | 69 | 660 | 10,000 |
| PEGD-2 | 700 | 78 | 655 | 20,000 |
| PEGD-3 | 703 | 81 | 656 | 30,000 |

Silicone—Extended Polyether Elastomer Preparation

To 89 g PDMS diamine was added 9.4 g PEGD-1 (50% solids in toluene) and 165 g THF. This was mixed until homogeneous then 6.8 g IPDI was added. This was mixed at 45° C. overnight to produce a 35% solids silicone-polyether elastomer, which contained approximately 5% (by weight) PEG in the polymer backbone. Additional elastomers were prepared as shown in Table 3. SPE-19 was prepared as a 25% solids mixture.

TABLE 3

Silicone - Extended Polyether Elastomer Preparation

| Silicone-Polyether Elastomer | PDMS Diamine (g) | PEG Diamine | (g) | % PEG in Polymer Backbone | IPDI (g) | THF Solvent (g) |
|---|---|---|---|---|---|---|
| SPE-1 | 89 | PEGD-1 | 9.4 | 5 | 6.8 | 165 |
| SPE-2 | 84 | PEGD-1 | 19 | 10 | 7.5 | 159 |
| SPE-3 | 80 | PEGD-1 | 28 | 15 | 8.2 | 154 |
| SPE-4 | 75 | PEGD-1 | 38 | 20 | 8.9 | 149 |
| SPE-5 | 65 | PEGD-1 | 56 | 30 | 10.3 | 138 |
| SPE-6 | 56 | PEGD-1 | 75 | 40 | 11.7 | 127 |
| SPE-7 | 89 | PEGD-2 | 9.4 | 5 | 6.3 | 165 |
| SPE-8 | 84 | PEGD-2 | 19 | 10 | 6.5 | 160 |
| SPE-9 | 80 | PEGD-2 | 28 | 15 | 6.7 | 155 |
| SPE-10 | 75 | PEGD-2 | 38 | 20 | 7.0 | 151 |
| SPE-11 | 66 | PEGD-2 | 56 | 30 | 7.4 | 141 |
| SPE-12 | 56 | PEGD-2 | 75 | 40 | 7.8 | 131 |
| SPE-13 | 89 | PEDG-3 | 9.4 | 5 | 6.2 | 165 |
| SPE-14 | 84 | PEDG-3 | 19 | 10 | 6.2 | 161 |
| SPE-15 | 80 | PEDG-3 | 28 | 15 | 6.3 | 156 |
| SPE-16 | 75 | PEDG-3 | 38 | 20 | 6.3 | 151 |
| SPE-17 | 66 | PEDG-3 | 56 | 30 | 6.5 | 142 |
| SPE-18 | 56 | PEDG-3 | 75 | 40 | 6.6 | 132 |
| SPE-19 | 148 | PEGD-2 | 16.4[a] | 7 | 11.3 | 525 |

[a]70% solids

Example 1 (E-1)

A silicone/extended polyether adhesive was prepared by mixing 21 g SPE-1 (35% solids), 9.7 g THF, and 1.6 g PEG. MQ resin (6.9 g) was added with further mixing. CHG (0.84 g at 20% solids) was added and the composition mixed until homogeneous. This was Example-1 (E-1).

E-2 Through E-18

E-2 through E-18 were prepared as in E-1 with the compositions shown in Table 4. Each composition contained 1.6 g PEG, and 0.84 g CHG.

Example 19

Example 19 was prepared by mixing 80 g SPE-19 (25% solids) with 2.2 g GMI. MQ resin (13.2 g) was added and composition mixed. Aqueous CHG (1.8 g at 20% solids) was added and the composition mixed until homogeneous.

E-20 Through E-26

E-20 through E-26 were prepared as in E-19 with the compositions shown in Table 5. Each composition contained 13.2 g MQ resin.

TABLE 4

Adhesive Formulations

| | Silicone-Polyether Elastomer | | THF | MQ |
|---|---|---|---|---|
| | | (g) | (g) | (g) |
| E-1 | SPE-1 | 21 | 9.7 | 6.9 |
| E-2 | SPE-2 | 21 | 9.3 | 6.7 |
| E-3 | SPE-3 | 22 | 9.0 | 6.5 |
| E-4 | SPE-4 | 23 | 8.6 | 6.3 |
| E-5 | SPE-5 | 24 | 7.7 | 5.8 |
| E-6 | SPE-6 | 26 | 6.7 | 5.3 |
| E-7 | SPE-7 | 21 | 9.7 | 6.9 |
| E-8 | SPE-8 | 21 | 9.3 | 6.7 |
| E-9 | SPE-9 | 22 | 9.0 | 6.5 |
| E-10 | SPE-10 | 23 | 8.6 | 6.3 |
| E-11 | SPE-11 | 24 | 7.7 | 5.8 |
| E-12 | SPE-12 | 26 | 6.7 | 5.3 |
| E-13 | SPE-13 | 21 | 9.7 | 6.9 |
| E-14 | SPE-14 | 21 | 9.3 | 6.7 |
| E-15 | SPE-15 | 22 | 9.0 | 6.5 |
| E-16 | SPE-16 | 23 | 8.6 | 6.3 |
| E-17 | SPE-17 | 24 | 7.7 | 5.8 |
| E-18 | SPE-18 | 26 | 6.7 | 5.3 |

TABLE 5

Adhesives Formulations with Additives

| | Silicone-Polyether Elastomer (g) | THF (g) | Additives (g) | | | | |
|---|---|---|---|---|---|---|---|
| | | | GMIS | Glycerol | SPAN 20 | PEG (g) | CHG (g) |
| E-19 | SPE-19 | 80 | 60 | 2.2 | 0 | 0 | 0 | 1.8 |
| E-20 | SPE-1 | 80 | 60 | 0 | 2.2 | 0 | 0 | 1.8 |
| E-21 | SPE-1 | 80 | 60 | 0 | 0 | 2.2 | 0 | 1.8 |
| E-22 | SPE-1 | 80 | 60 | 0 | 0 | 0 | 2.2 | 1.8 |
| E-23 | SPE-1 | 80 | 60 | 4.9 | 0 | 0 | 0 | 1.9 |
| E-24 | SPE-1 | 80 | 60 | 0 | 4.9 | 0 | 0 | 1.9 |
| E-25 | SPE-1 | 80 | 60 | 0 | 0 | 4.9 | 0 | 1.9 |
| E-26 | SPE-1 | 80 | 60 | 0 | 0 | 0 | 4.9 | 1.9 |

Example formulations were knife coated onto a fluorosilicone release liner (Loparex 5100, Cary, N.C.) at an 8 mil gap to give a 38 micron dry thickness. The adhesives were dried at 60° C. for 10 min and laminated onto polyurethane backing for testing.

Extended Silicone—Extended Polyether Adhesive Preparation

In a glass jar, 2.77 g of bis(trifluoroethyl)oxalate and 11.9 g anhydrous ethyl acetate were added and mixed on roller for about five minutes. To this mixture 25 g XTJ-578 was added. The contents were mixed on a roller for four days at ambient temp to produce an extended polyether. The SAEW of this 70% solids solution was approximately 10,700.

In a glass jar 2.24 g of bis(trifluoroethyl)oxalate and 402 g anhydrous ethyl acetate were added and mixed on a roller for about 5 minutes. To this mixture 400 g of 34 k silicone diamine (amine equivalent weight of 17,061) was added. The contents were mixed on a roller for four days at ambient temp to produce an extended silicone. The titrated SAEW of this 50% solids solution was approximately 137,480.

In a glass jar 27 g of the extended silicone, 2.14 g of the extended polyether, and 120.8 g of anhydrous ethyl acetate were added and mixed until homogeneous. To this mixture 0.5234 g of a 10% solution of H12MDI in toluene was added and the contents were mixed on a roller overnight to produce an extended silicone, extended polyether elastomer. MQ resin was mixed with this elastomer to produce adhesive examples as shown in Table 6.

TABLE 6

Extended silicone, Extended Polyether Adhesives

| Example | MQ (g) | MQ (weight %) | Extended silicone, Extended Polyether Elastomer (g) |
|---|---|---|---|
| E-27 | 0.3 | 10 | 27 |
| E-28 | 0.6 | 20 | 24 |
| E-29 | 0.9 | 30 | 21 |

Extended Silicone—Polyether Elastomer Preparation

In a glass jar 2.12 g bis(trifluoroethyl)oxalate and 322 g anhydrous ethyl acetate were added and mixed on a roller for about 5 minutes. To this mixture 320 g of 34 k silicone diamine (amine equivalent weight of 17,061) was added. The contents were mixed on a roller for four days at ambient temp to produce an extended silicone.

In a glass jar 49.2 g of the extended silicone, 0.188 g ED-2003, 17.3 g anhydrous isopropyl alcohol, and 32.0 g of anhydrous ethyl acetate were added and mixed until homogeneous. To this mixture 0.335 g of a 10% solution of IPDI in toluene was added and the contents were mixed on a roller overnight to produce an polyether, extended silicone elastomer. Triacetin (0.63 g) was added to 10 g of this elastomer were combined and mixed until homogeneous to produce an example elastomer with excipient. This was Example 30.

Results

Peel and microbial kill data are shown in Table 7.

TABLE 7

Test Results

| | Peel | Microbial (*S. aureus*) Kill (log) | |
|---|---|---|---|
| Example | (g/2.54 cm) | 2 hour | 24 hour |
| E-19 | 187 | 3.05 | 4.58 |
| E-20 | 215 | 4.38 | 4.78 |
| E-21 | 244 | 4.13 | 4.69 |
| E-22 | 272 | 3.75 | 4.69 |
| E-23 | 301 | 3.09 | 3.95 |
| E-24 | 329 | 4.59 | 4.78 |
| E-25 | 357 | 3.61 | 4.45 |
| E-26 | 386 | 4.74 | 4.54 |

Drug-in-Adhesive Formulations Preparation

Drug-in-adhesive formulations were prepared with lidocaine free base incorporated at 3, 5 and 6 weight percent in a silicone-polyether pressure-sensitive adhesive (Silicone/PEG Adhesive). Weight ratio of the first (Silicone) precursor to the second (polyether) precursor of Silicone/PEG Adhesive was 90:10 and Silicone/PEG Adhesive was composed of a 30% solids silicone-polyether copolymer in tetrahydrofuran. The silicone segment of the copolymer was composed of 70% polydimethylsiloxane and 30% MQ resin. Lidocaine was added directly to the solvated adhesive and rolled for 12 hours to ensure that the lidocaine was fully dissolved and uniformly dispersed. The solvated formulation was then knife coated on Scotchpak 9744 release liner (3M Company) using a knife gap of 0.019 inch. The resulting coatings were placed in a drying oven for 15 minutes at 60 degrees C. After removal from the oven, the dried coating weight for each sample was approximately 10 mg/cm². The dried coatings were laminated to CoTran 9722 polyethylene backing to form rollstock material and one cm² patches were then punched from the rollstock. The drug-in-adhesive patches were evaluated in vitro for skin permeation using human cadaver skin and a Franz Diffusion Cell. The conditions for the permeation study are detailed in Table 8.

TABLE 8

In Vitro Human Cadaver Skin Permeation - Experimental Conditions

Patch size: 1 cm²
Replicates: 5 per formulation
Skin: Dermatomed human cadaver skin (approximately 0.5 mm in thickness)
Receptor chamber solution composition: Phosphate buffer (pH 6.5)
Receptor chamber solution volume: 5 ml
Temperature: 32 degrees C.
Receptor sampling times: 3, 6, 9, 12, and 24 hours A comparative formulation was prepared at 5 weight percent lidocaine in an acrylic adhesive (93/7 isooctyl acrylate/acrylamide solvated in ethyl acetate/methanol) using the procedure described above.

Lidoderm® (Endo Pharmaceuticals, Malvern, Pa.) patches (5% lidocaine by weight) were die cut to one cm² and used as an experimental control.

Results

The delivery efficiency results from the permeation study are shown in Table 9.

TABLE 9

In Vitro Human Cadaver Skin Permeation Results

| Patch Description | Lidocaine Content (mg/cm²) | Average Cumulative Amount of Lidocaine Permeated in 12 hours (µg/cm²) (n = 5) | Delivery Efficiency (% of lidocaine that permeates in 12 hours) |
|---|---|---|---|
| 3% Lidocaine in Silicone/PEG Adhesive | 0.3 | 40.9 | 13.6% |
| 5% Lidocaine in Silicone/PEG Adhesive | 0.5 | 83.9 | 16.8% |
| 6% Lidocaine in Silicone/PEG Adhesive | 0.6 | 84.7 | 14.1% |
| 5% Lidocaine in Acrylic Adhesive | 0.5 | 25.7 | 5.1% |
| Lidoderm ® (5% Lidocaine) | 5.0 | 23.7 | 0.5% |

What is claimed is:

1. A pressure-sensitive adhesive comprising a copolymer, at least one of a tackifier and a plasticizer, and an active agent, the copolymer having a backbone composition comprising a first segment of Formula I:

$$\{X-W\}_b X- \qquad (I),$$

wherein X is a silicone; and
a second segment of a Formula of II:

$$\{Y-W\}_c Y- \qquad (II),$$

wherein Y is a polyether;
wherein W comprises at least one of an oxamide linkage and a urea linkage;

wherein b is an integer ranging from 2 to 30;
wherein c is an integer ranging from 3 to 30;
wherein the first segment and the second segment are connected via a urea linkage.

2. The pressure-sensitive adhesive of claim 1, wherein the pressure-sensitive adhesive comprises a plasticizer.

3. The pressure-sensitive adhesive of claim 1, further comprising an excipient.

4. The pressure-sensitive adhesive of claim 1, wherein the active agent is selected from estradiol, nicotine, nitroglycerine, clonidine, scopolamine, lidocaine, buprenorphine, rivastigmine, donepezil, fentanyl, sufentanil, testosterone, capsaicin, menthol, salicylic acid, oxybutynin, ethinyl estradiol, levonorgestrel, norethindrone, methylphenidate, selegiline, diclofenac, rotigotine, norelgestromin, granisetron, and combinations thereof.

5. The pressure-sensitive adhesive of claim 1, wherein the active agent includes an antimicrobial agent that comprises a quaternary ammonium salt.

6. The pressure-sensitive adhesive of claim 5, wherein the quaternary ammonium salt is selected from Chlorhexidine Gluconate (CHG), Polyhexamethylene Biguanide (PHMB), benzalkonium, benzethonium, Polydiallyldimethylammonium Chloride (polyDADMAC), homopolymers or copolymers comprising pendant quaternized ammonium moieties, and combinations thereof.

7. The copolymer of claim 1, wherein W comprises an oxamide linkage.

8. The copolymer of claim 1, wherein X comprises Formula III:

$$-R^3-\left[Si(R^1)(R^2)-O\right]_m-Si(R^1)(R^2)-R^4-, \quad (IV)$$

wherein each of $R^1$ and $R^2$ is independently selected from hydrogen; an alkyl group having from 1 to 10 carbons; and a phenyl group;
wherein each of $R^3$ and $R^4$ is independently selected from a linear or branched alkane, having from 1 to 10 carbons; and
wherein m is an integer ranging from 10 to 900.

9. The copolymer of claim 1, wherein Y comprises Formula V:

$$+R^5-O+_q \quad (V),$$

wherein $R^5$ is a linear or branched alkane, having from 1 to 10 carbons; and
wherein q is an integer ranging from 5 to 500.

10. The copolymer of claim 8, wherein Y comprises Formula V:

$$+R^5-O+_q \quad (V),$$

wherein $R^5$ is a linear or branched alkane, having from 1 to 10 carbons; and
wherein q is an integer ranging from 5 to 500.

11. The copolymer of claim 1, wherein X comprises Formula IV:

$$(IV)$$

wherein m is an integer ranging from 10 to 900.

12. The copolymer of claim 1, wherein Y comprises Formula VI:

$$(VI)$$

wherein x is an integer ranging from 2 to 60; and
wherein the sum of w and y is an integer ranging from 2 to 8.

13. The copolymer of claim 11, wherein Y comprises Formula VI:

$$(VI)$$

wherein x is an integer ranging from 2 to 60; and
wherein the sum of w and y is an integer ranging from 2 to 8.

* * * * *

UNITED STATES PATENT AND TRADEMARK OFFICE
CERTIFICATE OF CORRECTION

PATENT NO. : 10,329,384 B2
APPLICATION NO. : 15/025740
DATED : June 25, 2019
INVENTOR(S) : Richard Hansen et al.

It is certified that error appears in the above-identified patent and that said Letters Patent is hereby corrected as shown below:

In the Specification

Column 1
Line 31, Delete "seating," and insert -- sealing, --, therefor.

Column 4
Line 51, Delete "$\left[\!\!-\!R^5\!-\!O\!-\!\right]_q$ $_q$" and insert -- $\left[\!\!-\!R^5\!-\!O\!-\!\right]_q$ --, therefor.

Column 11
Line 51, Delete "$R^9SiO_{312}$" and insert -- $R^9SiO_{3/2}$ --, therefor.

Column 12
Line 67, Delete "an" and insert -- anti --, therefor.

Signed and Sealed this
Twenty-sixth Day of May, 2020

Andrei Iancu
*Director of the United States Patent and Trademark Office*